US012440635B2

(12) United States Patent
McKinney

(10) Patent No.: US 12,440,635 B2
(45) Date of Patent: Oct. 14, 2025

(54) SECUREMENT DEVICE FOR MEDICAL TUBING

(71) Applicant: Mackenzie McKinney, Powell, TN (US)

(72) Inventor: Mackenzie McKinney, Powell, TN (US)

(*) Notice: Subject to any disclaimer, the term of this patent is extended or adjusted under 35 U.S.C. 154(b) by 381 days.

(21) Appl. No.: 17/841,837

(22) Filed: Jun. 16, 2022

(65) Prior Publication Data

US 2023/0001121 A1 Jan. 5, 2023

Related U.S. Application Data

(60) Provisional application No. 63/217,577, filed on Jul. 1, 2021.

(51) Int. Cl.
*A61M 16/04* (2006.01)

(52) U.S. Cl.
CPC .............................. *A61M 16/0497* (2013.01)

(58) Field of Classification Search
CPC ................................................ A61M 16/0497
See application file for complete search history.

(56) References Cited

U.S. PATENT DOCUMENTS 3,993,081 A * 11/1976 Cussell ............. A61M 16/0488 128/207.14
4,270,529 A * 6/1981 Muto ................ A61M 16/0493 128/200.26
4,483,337 A * 11/1984 Clair ................. A61M 16/0488 128/207.17
4,774,944 A * 10/1988 Mischinski ....... A61M 16/0488 128/DIG. 26
5,233,979 A * 8/1993 Strickland ......... A61M 16/0497 128/207.14
5,345,931 A * 9/1994 Battaglia, Jr. ......... A61M 25/02 604/179
5,479,921 A * 1/1996 Reif ....................... A61M 25/02 128/DIG. 26
5,551,421 A * 9/1996 Noureldin ......... A61M 16/0488 604/179
5,803,079 A * 9/1998 Rogers .................. A61M 25/02 128/207.14
5,829,430 A * 11/1998 Islava ............... A61M 16/0493 128/207.14
5,894,840 A * 4/1999 King ................. A61M 16/0493 128/200.26

(Continued)

*Primary Examiner* — LaToya M Louis
(74) *Attorney, Agent, or Firm* — Chambliss, Bahner & Stophel, P.C.; Stephen D. Adams

(57) ABSTRACT

A medical securement device for use in securing a medical tube to a patient. The securement device includes a flat base having a top surface, a bottom surface configured to contact a skin surface of the patient, and a central circular opening formed in the flat base. The securement device further includes a cylindrical wall with an outer surface, an inner surface configured for placement adjacent the medical tube, a bottom end surrounding the central circular opening, a top end located opposite the bottom end. Adhesive is provided on the inner surface of the cylindrical wall and is configured to fix the medical tube at a selected position within the cylindrical wall such that a selected length of the medical tube extends below the bottom surface of the flat base.

17 Claims, 2 Drawing Sheets

(56) References Cited

U.S. PATENT DOCUMENTS

| | | | | | |
|---|---|---|---|---|---|
| 5,928,198 | A * | 7/1999 | Lester | A61M 16/0465 | 128/207.14 |
| 6,755,191 | B2 * | 6/2004 | Bertoch | A61M 16/0493 | 128/207.14 |
| 7,628,154 | B2 * | 12/2009 | Bierman | A61M 16/0493 | 128/206.27 |
| 2002/0026936 | A1 * | 3/2002 | Kirn | A61M 25/013 | 128/200.24 |
| 2002/0092526 | A1 * | 7/2002 | Bertoch | A61M 16/0497 | 128/206.29 |
| 2008/0202529 | A1 * | 8/2008 | Flory | A61M 16/0488 | 128/207.17 |
| 2012/0168571 | A1 * | 7/2012 | Bond | A61M 25/02 | 248/70 |
| 2014/0332009 | A1 * | 11/2014 | Haider | A61M 16/0497 | 128/207.14 |
| 2015/0018759 | A1 * | 1/2015 | Velez-Rivera | A61M 16/0409 | 604/79 |
| 2015/0297866 | A1 * | 10/2015 | Hyman | A61M 25/02 | 604/180 |
| 2016/0038703 | A1 * | 2/2016 | Islava | A61M 16/0497 | 128/200.26 |
| 2016/0074285 | A1 * | 3/2016 | Thomas | A61J 15/0053 | 604/174 |
| 2016/0129211 | A1 * | 5/2016 | Bruggemann | A61M 16/0497 | 128/207.14 |
| 2018/0154116 | A1 * | 6/2018 | Similowski | A61M 25/02 | |
| 2018/0344960 | A1 * | 12/2018 | Kaneyasu | A61M 16/0497 | |
| 2019/0070378 | A1 * | 3/2019 | Kanowitz | A61M 16/0497 | |
| 2019/0083729 | A1 * | 3/2019 | Bruggeman | A61M 16/0427 | |
| 2019/0290873 | A1 * | 9/2019 | Willett | A61M 16/0472 | |
| 2022/0241560 | A1 * | 8/2022 | Kanowitz | A61M 1/04 | |

* cited by examiner

SECUREMENT DEVICE FOR MEDICAL TUBING

REFERENCE TO RELATED APPLICATIONS

This application claims the benefit of U.S. Provisional Application No. 63/217,577 filed Jul. 1, 2021, and entitled "Securement Device for Medical Tubing," which is incorporated herein by reference in its entirety.

FIELD OF THE INVENTION

This invention relates generally to securement devices. More particularly, the present invention relates to a medical securement device for temporarily securing a portion of a tube within an insertion point of a medical patient's body.

BACKGROUND

In various instances in the medical field, one end of a medical device such as medical tubing, is inserted into an opening formed in a patient's skin and then the opposite end extends out through the opening. In many cases, the device is left in place for only a short period (e.g., hours or days). However, in other cases, it might be necessary to leave the device in place for a much longer time (e.g., days to weeks). One such device is a tracheostomy tube, which is a tube that may be inserted through a hole in a person's neck and then into the trachea to allow the person to breathe through the tube. Tracheostomy tubes are often used in conjunction with ventilators for long-term breathing assistance. Another device is a urinary catheter, which is a tube having one end that is inserted into the bladder and that allows urine to drain freely. There are several types of catheters, including both short-term and long-term catheters. A suprapubic catheter is a type of long-term catheter that may be left in place for several weeks. Rather than being inserted through the urethra like short-term (e.g., Foley) catheters, suprapubic catheters are inserted through a hole in the abdomen and then directly into the bladder.

In each case, the medical tubing is held in place by a device that permits the tubing to be removed and replaced as needed while also being securely held in place. One common securing method is with tape (or some other similar adhesive securement device), which is typically wrapped around the tube and then taped directly to the person's skin. Generally, the tape used to secure a catheter tube is spaced away from the opening/incision site. Then, gauze is separately taped over the insertion site in order to collect drainage, fluids, etc.

This type of securement method causes a number of problems. First, each time the device is replaced, cleaned, repositioned, etc., the tape is generally pulled off of the person's skin and is replaced with new tape. Over time, the repeated removal of tape from the skin can cause the skin to become irritated and to break down. Another problem with these conventional securing methods is that they do not fully secure the tube in place and an insufficient amount of holding force is provided at the incision site, which can allow leakages to occur around the insertion site. Additionally, since the medical tube is not secured at the insertion site, there is a possibility that the tube can move internally, which can cause irritation at the insertion site and can cause patient discomfort. This movement is also problematic because the tube could potentially be moved out of the optimal position and, therefore, become less effective over time.

What is needed, therefore, is a securement device for medical tubing and a method of use that assists in addressing the above-described issues.

Notes on Construction

The use of the terms "a", "an", "the" and similar terms in the context of describing embodiments of the invention are to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. The terms "substantially", "generally" and other words of degree are relative modifiers intended to indicate permissible variation from the characteristic so modified. The use of such terms in describing a physical or functional characteristic of the invention is not intended to limit such characteristic to the absolute value that the term modifies, but rather to provide an approximation of the value of such physical or functional characteristic.

Terms concerning attachments, coupling and the like, such as "attached", "connected" and "interconnected", refer to a relationship wherein structures are secured or attached to one another either directly or indirectly through intervening structures, as well as both moveable and rigid attachments or relationships, unless otherwise specified herein or clearly indicated as having a different relationship by context. The term "operatively connected" is such an attachment, coupling or connection that allows the pertinent structures to operate as intended by virtue of that relationship.

The use of any examples or exemplary language (e.g., "such as" and "preferably") herein is intended merely to better illuminate the invention and the preferred embodiments thereof, and not to place a limitation on the scope of the invention. Nothing in the specification should be construed as indicating any element as essential to the practice of the invention unless so stated with specificity.

SUMMARY

The above and other problems are addressed by a medical securement device for use in securing a medical tube to a patient. The securement device includes a flat base having a top surface, a bottom surface configured to contact a skin surface of the patient, a central circular opening formed in the flat base. The device further includes a cylindrical wall having an outer surface, an inner surface configured for placement adjacent the medical tube, a bottom end surrounding the central circular opening, and a top end located opposite the bottom end. Adhesive is provided on the inner surface of the cylindrical wall and is configured to fix the medical tube at a selected position within the cylindrical wall such that a selected length of the medical tube extends below the bottom surface of the flat base.

In certain embodiments, the device further includes a first slot opening formed in the flat base that extends from the central circular opening to a periphery of the flat base. Additionally, a second slot opening extends from the bottom end of the cylindrical wall to the top end of the cylindrical wall. The first slot opening is joined together continuously with the second slot opening to form a continuous slot that extends along the flat circular base and the cylindrical wall. The continuous slot provides separable sides located adjacent either side of the continuous slot such that the circular wall can be widened or narrowed by moving the separable sides closer together or further apart in order to at least partially encircle the medical tube and where the medical tube has an outside diameter that is within a range of outside diameters that work with the securement device. In certain embodiments, the first slot opening expands and is wider at the periphery of the flat base than at the central circular opening.

In certain embodiments, the device includes a suture aperture in the flat base that is sized and configured to receive suture material that may be used in suturing the securement device to the patient. Preferably a suture aperture is located proximate each side of the continuous slot. Certain embodiments provide a plurality of suture apertures in the flat base along an entirety of the cylindrical wall, and each suture aperture is sized and configured to receive suture material used in suturing the securement device to the patient.

In certain embodiments, adhesive is provided exclusively on the inner surface of the cylindrical wall. In some embodiments, the securement device further includes an adhesive cover that is removably placed over the adhesive. The adhesive cover prevents contact with the adhesive such that the adhesive cover must be removed in order to make contact with the adhesive. In certain cases, a removal tab is provided on the adhesive cover and is sized to be grasped by a user for assisting in the removal of the adhesive cover from the adhesive. In preferred embodiments, the removal tab extends away from the top end of the cylindrical wall.

Also disclosed herein is a securement method that requires the steps of providing a medical tube and providing a securement device. The securement device includes a flat base having a top surface, a bottom surface, a central circular opening formed in the flat base. The securement device further includes a cylindrical wall having an outer surface, an inner surface, a bottom end surrounding the central circular opening of the flat base, and a top end located opposite the bottom end. An adhesive is provided on the inner surface of the cylindrical wall and is not located on the bottom surface of the flat base. The method also includes the step of placing a portion of the medical tube in a space within the cylindrical wall such that the inner surface of the cylindrical wall is adjacent an outer surface of the medical tube. Then, at a selected position within the cylindrical wall, the outer surface of the medical tube is contacted with the adhesive on the inner surface of the cylindrical wall such that a selected length of the medical tube extends below the bottom surface of the flat base. Next, the selected length of the medical tube is inserted into an opening formed in a skin surface of a patient. Finally, the securement device is fixed in place such that the bottom surface of the base operatively contacts the skin surface adjacent the opening formed in the skin.

In certain cases, the medical tube is a catheter having an inflatable balloon. In those cases, the method preferably further includes the step of inserting the medical tube sufficiently through the skin surface that the inflatable balloon rests below the skin surface and then fixing the securement device by inflating the inflatable balloon. In certain embodiments of the method, the securement device includes a suture aperture in the flat base. In those cases, the method preferably further includes the step of suturing the securement device to the skin surface by passing suture material through the suture aperture and through the skin surface. In certain cases, when the securement device is fixed in place, either by a balloon or a suture or by other means, the flat base exerts a constant pressure force on the skin surface. Preferably, the constant pressure force is sufficient to arrest bleeding caused by the insertion of the medical tube through the opening in the skin of the patient.

In certain embodiments of the method, the securement device further includes a first slot opening formed in the flat base that extends from the central circular opening to a periphery of the flat base. Additionally, a second slot opening extends from the bottom end of the cylindrical wall to the top end of the cylindrical wall. Preferably, the first slot opening is joined together continuously with the second slot opening to form a continuous slot that extends along the flat circular base and the cylindrical wall in order to provide separable sides located adjacent either side of the continuous slot such that the space within the circular wall can be increased or decreased by moving the separable sides closer together or further apart. In certain cases, the method includes the step of moving the separable sides of the circular wall to resize the space within the cylindrical wall. In certain cases, the method includes the step of placing a portion of the medical tube within the cylindrical wall by inserting the medical tube through the continuous slot.

BRIEF DESCRIPTION OF DRAWINGS

Further advantages of the invention are apparent by reference to the detailed description when considered in conjunction with the figures, which are not to scale so as to more clearly show the details, wherein like reference numerals represent like elements throughout the several views, and wherein.

DETAILED DESCRIPTION

Figure 1:
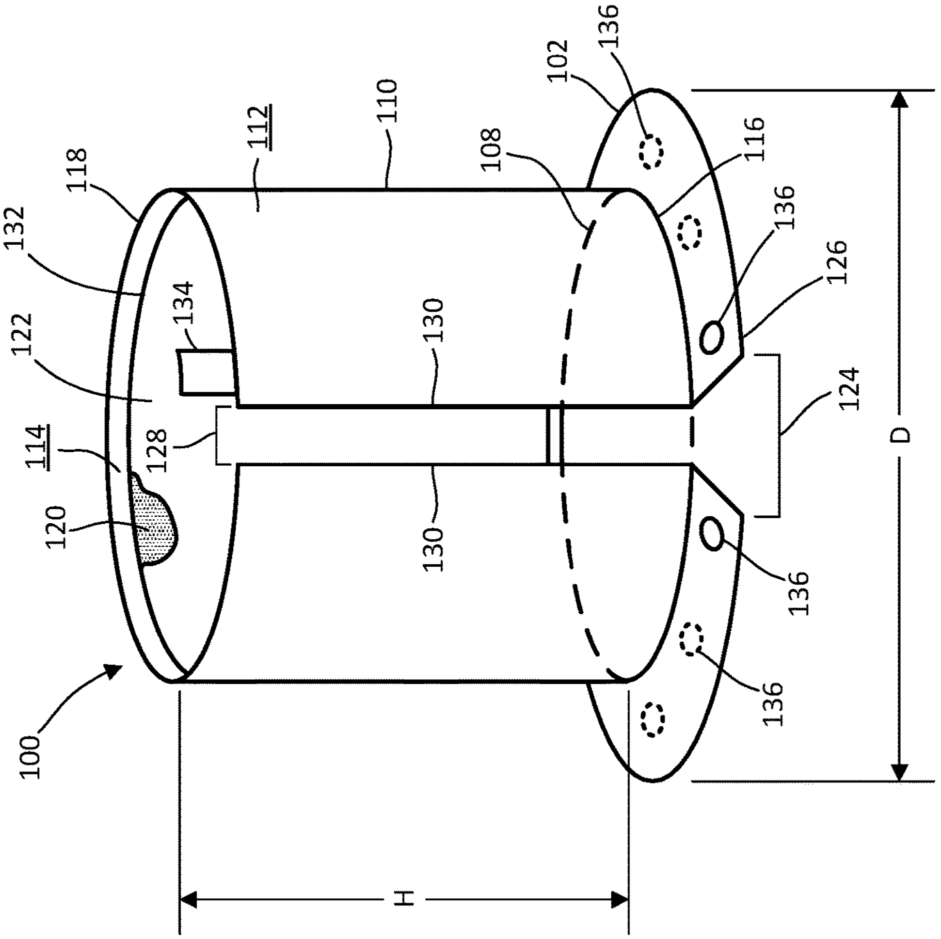
FIG. 1 is a front perspective view illustrating a securement device according to an embodiment of the present disclosure.
Figure 3:
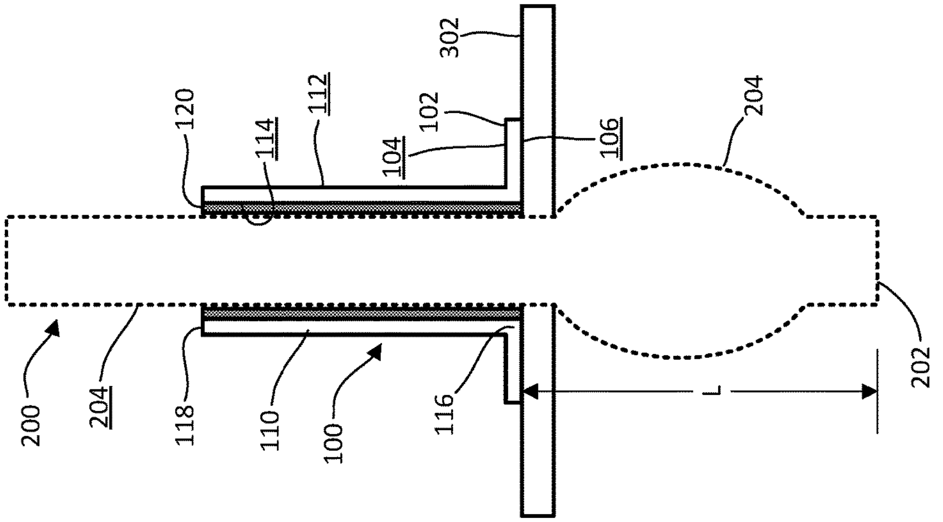
FIG. 3 is a sectional view of the securement device of FIG. 1 fitted to a medical tube that is inserted into a patient and then secured via an inflatable balloon placed below a skin surface.
Figure 2:
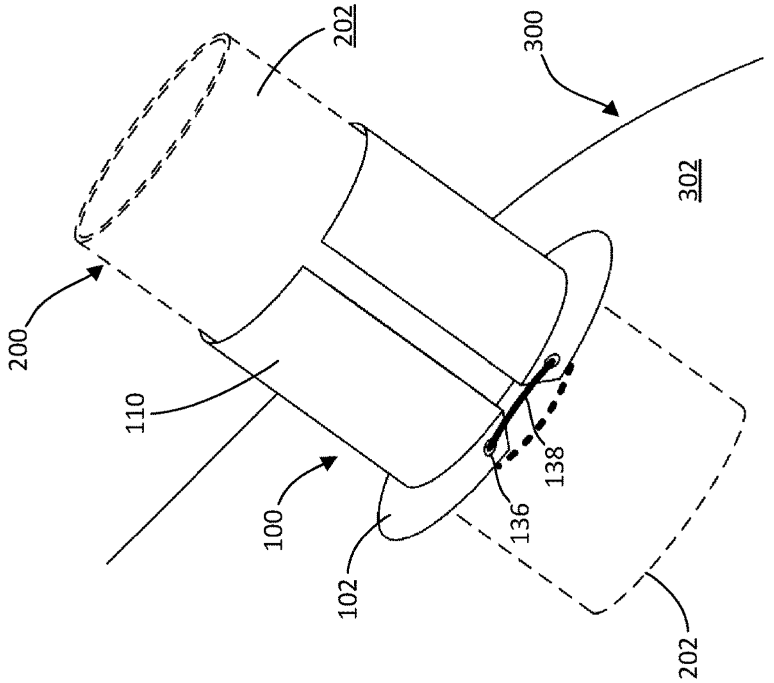
FIG. 2 is a perspective view illustrating the securement device of FIG. 1 fitted to a medical tube that is inserted into a patient and then secured via a suture.

Referring now to the drawings in which like reference characters designate like or corresponding characters throughout the several views, there is shown in FIGS. 1-3, there is provided a medical securement device 100 for use in securing a tube-like structure, such as a catheter tube, chest tube, gastric tube, or abscess tube, to a patient 300 according to an embodiment of the present invention. The term "medical tube" 200 is used generally throughout this description to refer to all such tube-like structures that may be secured to a patient 300 using securement device 100.

The securement device 100 includes a flat base 102 having a top surface 104, a bottom surface 106 configured to contact a skin surface 302 of the patient, and a central circular opening 108 formed in the flat base. A cylindrical wall 110 having an outer surface 112, an inner surface 114 configured for placement adjacent the medical tube 200, a bottom end 116 surrounding the central circular opening 108, and a top end 118 located opposite the bottom end. Adhesive 120 is provided on the inner surface 114 of the cylindrical wall 110 and is configured to adhere to and to fix the medical tube 200 at a selected position within the cylindrical wall such that a selected length L of the medical tube extends below the bottom surface 106 of the flat base 102 and the skin surface 302. Also disclosed is a method for using the securement device 100 described above for the purpose of fixing or securing a medical tube 200 to a patient 300. More particularly, securement device 100 is useful for securing and stabilizing a medical tube 200 to a patient 300, where a length L of the medical tube extends through the skin surface 302 of the patient. This might include, for example, a catheter such as a suprapubic catheter, a chest tube, or other similar medical tubes. The securement device 100 may also be used in other situations for securing and stabilizing other tubes, including where the tube does not pass through an opening formed in a patient's skin.

When the securement device 100 is used, an end 202 of the medical tube 200 is usually first inserted through an opening or incision (not shown) in the skin surface 302 of the patient 300 so that a selected length L of the medical tube extends below the bottom surface 106 of the flat base 102 and the skin surface 302. Once the medical tube 200 has been correctly located, a portion of the medical tube 200 is placed into a space 122 formed within the cylindrical wall 110 such that the inner surface 114 of the cylindrical wall 110 is adjacent an outer surface 202 of the medical tube. The height H of the cylindrical wall 110, measured from bottom end 116 to top end 118, should be tall enough to allow for sufficient contact between the cylindrical wall and the medical tube 200 that a leak-proof seal can be formed. However, the cylindrical wall 110 should not be so tall that it interferes with clothing or movement of the patient.

In certain embodiments, the free end of the medical tube 200 (i.e. the end that has not been inserted through the skin surface 302) may be inserted through the central circular opening 108 of the securement device. In other embodiments, the securement device 100 includes a first slot opening 124 that formed in the flat base 102 and that extends from the central circular opening 108 to a periphery 126 of the flat base. Additionally, a second slot opening 128 extends from the bottom end 116 of the cylindrical wall 110 to the top end 118 of the cylindrical wall. The first slot opening 124 is joined together continuously with the second slot opening 128 to form a continuous slot that extends along the flat circular base and the cylindrical wall. This, in turn, provides separable sides 130 located adjacent either side of the continuous slot such that the cylindrical wall 110 can be widened or narrowed by moving the separable sides closer together or further apart. This continuous slot allow for the separable sides 130 to be opened and for the securement device 100 to be placed around and to fully or partially encircle the medical tube 200. In certain embodiments, the first slot opening 124 expands or flares and is wider at the periphery 126 than it is at the central circular opening 108. This expansion of the first slot opening 124 may assist in more quickly and accurately placing the securement device 100 around the medical tube 200. In particular, when in use, the slanted sides that form the flared slot opening 124 would tend to slide along the outer surface of the medical tube 200 and the automatically open the continuous slot to allow the medical tube to more quickly and easily be positioned within the cylindrical wall 200.

Advantageously, the separable sides 130 allow for the space 122 within the cylindrical wall 110 to be increased or decreased in order to accommodate medical tubes 200 having a range of outer diameters. Thus, the same sized securement device 100 may be used in conjunction with a range of medical tube sizes. Whether the medical tube 200 is partially or fully encircled by the cylindrical wall 110 depends on the circumference of the cylindrical wall and the outer diameter of the medical tube. Preferably, the cylindrical wall 110 surrounds at least a majority of the outer perimeter of the medical tube 200.

Next, the outer surface 202 of the medical tube 200 is placed into contact with the adhesive 120 that is located on the inner surface 114 of the cylindrical wall 110 in order adhere the securement device 100 to the medical tube such that the selected length L of the medical tube extends below the bottom surface 106 of the flat base 102. Importantly, no adhesive is provided on the bottom surface 106 of the flat base 102. As a result, there is no adhesion between the securement device 100 and the patient. Advantageously, this avoids the skin irritation issues that are common when securing medical tubes using conventional methods. In certain embodiments, adhesive is provided exclusively on the inner surface 114 of the cylindrical wall 110. In certain preferred embodiments, a removable adhesive cover 132 is placed over the adhesive, prevents inadvertent contact with the adhesive, and must be removed in order to make contact with the adhesive. In FIG. 1, a portion of the cover 132 is removed in order to illustrate the adhesive 120 that lies below the adhesive cover. The adhesive cover 132 may also be provided with a removal tab 134 that is formed integrally with the cover and is sized to be grasped by a user for assisting in the removal of the adhesive cover from the adhesive 120. In preferred embodiments, the removal tab 134 extends upwards away from the top end 118 of the cylindrical wall 110. Preferably, adhesive 120 can be easily removed with a solvent, such as isopropyl alcohol, such that the medical tube 200 can be selectively removed from the securement device.

Preferably, when the securement device 100 and medical tube 200 are attached to one another, the securement device is positioned such that the bottom surface 106 of the flat base 102 is in direct or indirect contact with the skin surface 302 of the patient 300 and surrounds the opening in the skin surface. For that reason, securement device 100, as a whole or at least flat base 102 are preferably formed using a medical grade or biocompatible material, such as a medical-grade silicone, which will is suitable for contact with the skin surface 302. Preferably, the flat base is formed from a stiff enough material and is sized with a diameter D that is sufficiently large to significant movement of the medical tube 200 at the incision site.

Preferably, the securement device 100 is then fixed in place such that the flat base 102 exerts a constant pressure force on the skin surface 302 directly at the incision site. Even more preferably, the constant pressure force is sufficient to arrest bleeding caused by the insertion of the medical tube 200 through the opening. Additionally, gauze (not shown) may be placed with the securement device 100 around the incision site in order to further reduce and absorb blood or other fluids.

There are several ways that the securement device 100 can be secured to the skin surface 302 in the selected location to provide the desired amount of constant pressure. For example, as shown in FIGS. 1 and 2, the securement device 100 may include a suture aperture 136 in the flat base 102 that is sized and configured to receive suture material 138 used in suturing the securement device to the patient. In preferred embodiments, a suture aperture 136 is located in the flat base 102 proximate each side of the continuous slot 124/128. A separate suture 138 may be passed through each aperture 136 or, as illustrated in FIG. 2, a single suture may be passed through both apertures. In still other embodiments, the securement device may include multiple apertures 136 in the flat base 102. In those cases, the apertures 136 preferably extend around the entirety of the cylindrical wall 110. Again, each suture aperture is sized and configured to receive suture material 138 for use in securing the securement device 100 to the patient 300. In other cases, suturing is not required when stabilization is provided through other means. For example, as shown in FIG. 3, certain medical tubes 200, including certain catheters, include inflatable balloons 204 located at one end. Usually, after the end of the tube 200 having the balloon 204 is inserted into a patient, the balloon may be inflated in order to keep the tube in place. This same procedure may be used with the securement device 100. In use, the end 202 of the tube 200 with the balloon 204 is inserted sufficiently far through the skin surface 302 that the balloon rests below the skin surface. The balloon 204 is inflated in order to fix and stabilize the medical tube 200.

Although this description contains many specifics, these should not be construed as limiting the scope of the invention but as merely providing illustrations of some of the presently preferred embodiments thereof, as well as the best mode contemplated by the inventor of carrying out the invention. The invention, as described herein, is susceptible to various modifications and adaptations as would be appreciated by those having ordinary skill in the art to which the invention relates.

The invention claimed is:

1. A medical securement device for use in securing a medical tube that has an outer diameter to a patient, the securement device comprising:

a flat base having a periphery, an inner edge, a top surface, a bottom surface, and a central circular opening formed in the flat base and defined by the inner edge, wherein the inner edge of the central circular opening is configured to immediately surround and to contact the medical tube, wherein the bottom surface of the flat base extends continuously between the periphery and the inner edge of the central circular opening, and wherein the bottom surface is configured to contact and to lay flat against a skin surface of the patient continuously between the periphery and the inner edge of the flat base;

a cylindrical wall having an outer surface, an inner surface configured to immediately surround and to contact the medical tube, a bottom end joined continuously to the flat base along an entirety of the inner edge such that the flat base and the cylindrical wall are formed as a single unitary component with the flat base extending outwards from the bottom surface of the cylindrical wall, and a top end located opposite the bottom end;

a continuous slot opening extending continuously along the flat base and the cylindrical wall to provide a pair of separable sides along each side of the slot;

a space formed within the cylindrical wall, wherein a diameter of the space is defined by the cylindrical wall and wherein the securement device is formed from a material configured to allow the separable sides to move towards or away from one another such that the diameter of the space may be resized within a continuous range of sizes in order to receive medical tubes having a range of outer diameters that correspond to the diameter of the space and such that, when the securement device is in use, the inner edge of the flat base and the inner surface of the cylindrical wall, from the bottom end to the top end, makes continuous contact with medical tube; and adhesive provided on the inner surface of the cylindrical wall and configured to fix the medical tube at a selected position within the cylindrical wall such that a selected length of the medical tube extends below the bottom surface of the flat base.

2. The securement device of claim 1 further comprising a suture aperture in the flat base that is sized and configured to receive suture material used in suturing the securement device to the patient.

3. The securement device of claim 1 wherein a suture aperture is located proximate each side of the continuous slot.

4. The securement device of claim 1 further comprising a plurality of suture apertures in the flat base along an entirety of the cylindrical wall, wherein each suture aperture is sized and configured to receive suture material used in suturing the securement device to the patient.

5. The securement device of claim 1 wherein the continuous slot comprises a first slot opening disposed in the flat base that is joined continuously with a second slot opening disposed in the cylindrical wall, wherein the first slot opening expands and is wider at the periphery of the flat base than at the central circular opening.

6. The securement device of claim 1 wherein the adhesive is provided exclusively on the inner surface of the cylindrical wall.

7. The securement device of claim 1 wherein the securement is formed as a single unitary component.

8. The securement device of claim 1 wherein the cylindrical wall is configured to be fixed to the medical tube without requiring the separable sides along each side of the slot to be joined together such that the securement can be adhered to the medical tube while partially or fully encircling the medical tube.

9. The securement device of claim 1 wherein an entirety of the cylindrical wall is deformable such that a spacing between the separable sides may be selectively increased and decreased in order to increase and decrease, respectively, the diameter of the space within a continuous range of sizes, wherein the securement is further configured to be connected to the medical tube while partially or fully encircling the medical tube and without requiring the separable sides to be joined together by adhering the cylindrical wall at the selected size to the medical tube, including while the cylindrical wall partially encircles the medical tube or fully encircles the medical tube.

10. A securement method comprising the steps of:

providing a medical tube having an outer diameter;

providing a securement device comprising:

a flat base having a periphery, an inner edge, a top surface, a bottom surface, a central circular opening formed in the flat base and defined by the inner edge, wherein the inner edge of the central circular opening is configured to immediately surround and to contact the medical tube, wherein the bottom surface of the flat base extends continuously between the periphery and the inner edge of the central circular opening, and wherein the bottom surface is configured to contact and to lay flat against a skin surface of a patient continuously between the periphery and the inner edge of the flat base; and a cylindrical wall having an outer surface, an inner surface configured to immediately surround and to contact the medical tube, a bottom end joined continuously to the flat base along an entirety of the inner edge of the flat base such that the flat base and the cylindrical wall are formed as a single unitary component with the flat base extending outwards from the bottom surface of the cylindrical wall, and a top end located opposite the bottom end;

a continuous slot opening extending continuously along the flat base and the cylindrical wall to provide a pair of separable sides along each side of the slot;

a space formed within the cylindrical wall, wherein a diameter of the space is defined by the cylindrical wall and wherein the securement device is formed from a material configured to allow the separable sides to move towards or away from one another such that the diameter of the space may be resized within a continuous range of sizes in order to receive medical tubes having a range of outer diameters that correspond to the diameter of the space and such that, when the securement device is in use, the inner edge of the flat base and the inner surface of the cylindrical wall, from the bottom end to the top end, makes continuous contact with medical tube; and adhesive provided on the inner surface of the cylindrical wall and not located on the bottom surface of the flat base;

placing a portion of the medical tube in the space within the cylindrical wall such that the inner edge of the flat base and the inner surface of the cylindrical wall, from the bottom end to the top end, makes continuous contact with an outer surface of the medical tube;

contacting the outer surface of the medical tube with the adhesive on the inner surface of the cylindrical wall such that the medical tube is adhered to the cylindrical wall and a selected length of the medical tube extends below the bottom surface of the flat base;

inserting the selected length of the medical tube into an opening formed in a skin surface of a patient;

fixing the securement device such that the bottom surface of the base operatively lays flat and continuously contacts the skin surface of the patient continuously between the periphery and the central circular opening of the flat base.

11. The method of claim 10 wherein the medical tube is a catheter having an inflatable balloon, the method further comprising the steps of:

inserting the medical tube sufficiently through the skin surface that the inflatable balloon rests below the skin surface; and fixing the securement device by inflating the inflatable balloon.

12. The method of claim 10 wherein the securement device comprises a suture aperture in the flat base, the method further comprising the step of suturing the securement device to the skin surface by passing suture material through the suture aperture and through the skin surface.

13. The method of claim 10 wherein, when the securement device is fixed in place, the flat base exerts a constant pressure force on the skin surface.

14. The method of claim 13 wherein the constant pressure force is sufficient to arrest bleeding caused by the insertion of the medical tube through the opening.

15. The method of claim 10 further comprising the step of moving the separable sides of the circular wall to resize the space within the cylindrical wall.

16. The method of claim 10 further comprising the step of placing a portion of the medical tube within the cylindrical wall by inserting the medical tube through the continuous slot.

17. A securement for securing a medical tube having an outer diameter to a patient, the securement comprising:

a base defined by a periphery and an inner edge, wherein the inner edge has a diameter that defines a central circular opening;

a flat bottom surface that extends continuously between the periphery and the inner edge of the base, wherein the flat bottom surface is configured to conform to the patient such that an entirety of the bottom surface between the periphery and the inner edge is configured to operatively rest against the patient when the securement is in use;

a cylindrical wall integrally formed with the base and extending upwards from the base continuously along an entirety of the inner edge;

a size-adjustable cylindrical space that is formed within the cylindrical wall and that has an outer diameter defined by an inner surface of the cylindrical wall, wherein the space is sized and configured to receive a portion of the medical tube;

a slot opening extending continuously along the base and the cylindrical wall to provide a pair of separable sides along each side of the slot, wherein the outer diameter of the size-adjustable cylindrical space is continuously adjustable by moving one of the separable sides towards or away from the other separable side; and an adhesive disposed exclusively on the inner surface of the cylindrical wall for adhering the securement to the medical tube, wherein, when the cylindrical wall of the securement is adhered to the medical tube, the diameter of the inner edge and the outer diameter of the cylindrical space is approximately equal to the outer diameter of the medical tube such that the inner edge of the flat bottom and the inner surface of the cylindrical wall is in continuous contact with the medical tube.

* * * * *